United States Patent
Bermejo et al.

(10) Patent No.: US 6,300,307 B1
(45) Date of Patent: Oct. 9, 2001

(54) SOFTENING ACTIVE SUBSTANCE FOR TEXTILES AND TEXTILES-SOFTENING COMPOSITIONS CONTAINING IT

(75) Inventors: María José Bermejo; Marisa Mumbrú ; Josep Vilaret, all of Barcelona (ES)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/403,762

(22) PCT Filed: Apr. 24, 1998

(86) PCT No.: PCT/JP98/01914

§ 371 Date: Nov. 1, 1999

§ 102(e) Date: Nov. 1, 1999

(87) PCT Pub. No.: WO98/49132

PCT Pub. Date: Nov. 5, 1998

(30) Foreign Application Priority Data

Apr. 30, 1997 (ES) .................................... 9700933

(51) Int. Cl.⁷ ................................ C11D 1/62; C11D 1/66
(52) U.S. Cl. ........................ 510/499; 510/504; 510/515
(58) Field of Search ................................... 510/504, 499, 510/515

(56) References Cited

U.S. PATENT DOCUMENTS

| 4,405,471 | * | 9/1983 | Manson et al. ..................... 252/35 |
| 4,767,547 | * | 8/1988 | Straathof et al. . |
| 5,916,863 | * | 6/1999 | Iacobucci et al. . |
| 6,004,913 | * | 12/1999 | Iacobucci et al. . |
| 6,037,315 | * | 3/2000 | Franklin et al. . |

FOREIGN PATENT DOCUMENTS

| 25 00 241 A | | 7/1976 | (DE) . |
| 19539846 | * | 11/1996 | (DE) . |
| 0770 594 A1 | | 10/1996 | (EP) . |
| 602 048 A | | 5/1948 | (GB) . |

\* cited by examiner

*Primary Examiner*—John Hardee
(74) *Attorney, Agent, or Firm*—Oblon, Spivak, McClelland, Maier & Neustadt P.C.

(57) ABSTRACT

Substances for the preparation of textile softening compositions comprising salts of oligomeric amine esters obtained by the reaction of triethanolamine, fatty acids and dicarboxylic acids in defined ratios, optionally followed by quaternization. Textile softening compositions comprising these substances are also described.

26 Claims, No Drawings

SOFTENING ACTIVE SUBSTANCE FOR TEXTILES AND TEXTILES-SOFTENING COMPOSITIONS CONTAINING IT

TECHNICAL FIELD

The present invention relates to a new active substance for the preparation of textile-softening compositions which is constituted by salts of oligomeric amine esters obtained by the reaction of triethanolamine with fatty acids and dicarboxylic acids in defined ratios, and/or by the corresponding quaternised compounds thereof, and also to the textile-softening compositions containing it.

PRIOR ART

Compounds generally known by the generic name of esterquats are cationic surfactants which are used, inter alia, in the field of softening textile fibres. Chemically, they are esters of polyhydroxy-alkylamines and fatty acids subsequently quaternised with different types of alkylating compounds, for example, methyl choride, dimethyl sulphate, dimethyl carbonate. Their main advantage is their high degree of biodegradability, a characteristic which renders them especially suitable for large-scale use owing to their low-level contribution to environmental pollution.

The esterquats most commonly used for that purpose include a) quaternised diesters of fatty acids with 1,2-dihydroxy-3-dimethylaminopropane, as described in U.S. Pat. No. 4,137,180 and EP-A-0585040, the most commonly used product of this type being that corresponding to the diester of hydrogenated tallow fatty acid quaternised with methyl chloride, b) the quaternised dijesters of fatty acids with N-methyldiethanolamine, such as those described in FR-A-1593921 and in EP-B-0239910, the most commonly used product of this type being that corresponding to the diester of tallow fatty acid quaternised with methyl chloride, and c) the quaternised diesters of fatty acids with triethanolamine, such as those described in U.S. Pat. No. 3,915,867, the most commonly used product of this type being that corresponding to the diester of partially hydrogenated tallow fatty acid quaternised with dimethyl sulphate.

It should be noted that reference to the term "diester" is intended to mean that the diester predominates in the mixture, although the product may contain variable amounts of monoester compounds and, in the case of triethanolamine, of triester compounds.

The esterquats of group C), that is to say, those derived from triethanolauine, are those which are undergoing major development at present owing to the advantages they provide in respect of ease of handling and greater ease of dispersion in water.

EP-A-770594 corres ponding to DE-C-19539846, describes a new type of esterquat which is obtained by esterification of trialkanolamines wi th a mixture of fatty acids and dicarboxylic acids, optionally followed by alkoxylation of the product mixture obtained, and subsequent quaternisation with an alkylating agent. According to the mentioned patent, the esterquats so obtained exhibit excellent behaviour as conditioning agents for fibres and hair and they have a better ecotoxicological tolerance than do previously known esterquats.

Although the patent mentions the possible application of the products as conditioning and anti-static agents for natural and synthetic fibres, in fact all of the description and the Examples thereof relate to their application as hair-conditioning agents in products for personal hygiene (shower and bath gels, shampoos, etc.), no specific information being provided on their use as textile fibre softeners. In fact, if the molar ratios defined as preferred or the molar ratios used in the Examples are employed for application as softening agents for textile fibres, softness results are unfavourable compared with those conventional esterquats mentioned above are used.

Finally, BE-A-837285 describes liquid mixtures of surface-active hydroxy esters obtained by reacting 1 mole of a polyol, triehanolamine being among those mentioned, with from 1 to 2 moles of a $C_{16}$–$C_{26}$ saturated fatty acid and from 0.1 to 0.7 moles of a $C_3$–$C_{10}$ aliphatic dicarboxylic acid. The ester mixtures are not quaternised and are not converted into salts and are used as emulsifiers in the preparation of fibres or lubricants, and also in the cosmetic and pharmaceutical fields.

Hitherto, therefore, no solution has been found to the problems involved in the application to the field of textile-softeners of surfactants obtained by the esterification of triethanolamine with a mixture of fatty acids and dicarboxylic acids, nor to the problems presented by the esterquats produced by the quaternisation thereof.

DISCLOSURE OF THE INVENTION

The present invention solves those problems in that, while preserving the excellent biodegradability properties of the mentioned type of product, it provides a new active substance for the preparation of textile-softening compositions which are more efficient as regards their softening effect for textiles.

Consequently, the object of the present invention is to provide a new active substance for the formulation of textile-softening compositions which, while maintaining a high level of ecological tolerance, is highly efficient in its fabric-softening effect.

Another aim of the present invention is to provide new textile-softening compositions which contain said active substance.

The invention provides a textile-softening agent and an active substance for a textile-softening composition, comprising (a) a salt of an oligomeric amine ester obtained by esterifying triethanolamine with a mixture of a fatty acid and an aliphatic dicarboxylic acid at a molar ratio of the sum in total of the fatty acid and the dicarboxylic acid to triethanolamine ranging from 1.6:1 to 2.5:1 at a molar ratio of the fatty acid to the aliphatic dicarboxylic acid ranging from 2.2:1 to 11:1 or (b) a quaternized product of the oligomeric amine ester as defined above.

It is preferable that the esterification is conducted at a molar ratio of the sum in total of the fatty acid and the dicarboxylic acid to triethanolamine ranging from 1.6:1 to 2.5:1 at a molar ratio of the fatty acid to the aliphatic dicarboxylic acid ranging from 2.5:1 to 10:1.

It is more preferable that a molar ratio of the sum in total of the fatty acid and the dicarboxylic acid to triethanolamine ranges from 1.9:1 to 2.2:1 and a molar ratio of the fatty acid to the aliphatic dicarboxylic acid ranges from 2.5:1 to 10:1 or from 2.5:1 to 4.5:1.

The softener of the invention may comprise both (a) and (b). The invention provides use of (a) or (b) for textile-softener and a composition comprising (a) or (b).

The fatty acids which may be used for the purposes of the present invention are carboxylic acids of the general formula R—COOH, wherein R is a linear or branched hydrocarbon chain having from 7 to 23 carbon atoms which is completely saturated or which has one or more unsaturated moieties. Both acids obtained from completely or partially hydrogenated vegetable or animal oils and fats, for example those of coconut, tallow, palm, rape-seed, sunflower, etc., and purified fatty acids, such as lauric acid, stearic acid, palmitic acid, oleic acid, etc., may be used.

Aliphatic dicarboxylic acids suitable for the purpose of the invention are those corresponding to the general formula

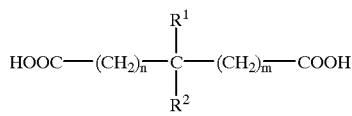

wherein m and n are, independently of one another, integers from 0 to 17 and $R^1$ and $R^2$ represent, independently of one another, a hydrogen atom or a $(CH_2)_p CH_3$ group, p being 0 to 17.

Non limiting preferred examples of this type of acid include adipic acid, sebac.ic acid, suberic acid, and also those known as dimeric fatty acids which are obtainable by thermal oligomerisation of unsaturated fatty acids, such as those marketed by Unichema International under the tradename, PRIPOL.

The products constituting the softening active substance of the present invention are obtained by procedures known per se which are used in the preparation of conventional esterquats and which are also described in DE-C-19539846.

Thus, for example, the esterification reaction can be effected by condensing the triethanolamine with a mixture of the fatty acids and the aliphatic dicarboxylic acid, at a temperature of from 120° C. to 220° C. for a period of from 2 to 10 hours, preferably under a reduced pressure of approximately from 5 to 200 mbar, in the presence of one of the catalysts already known for the esterification of conventional esterquats, for example hypophosphorous acid or paratoluenesulphonic acid and also in the presence of one of the customary stabilisers and antioxidants such as tocopherols, BHT, BHA and citric acid. The reaction is complete when the acidity index of the reaction mixture is lower than 12 mg KOH/g, preferably lower than 6 mg KOH/g. As will be appreciated by the expert, the esterification reaction can alternatively be effected by condensing the triethanolamine first with the fatty acids and then with the dicarboxylic acids, or by condensing the amine first with the dicarboxylic acids and then with the fatty acids.

The amine esters obtained exhibit a specific degree of oligomerisation compared with the units of initial triethanolamine which are incorporated in each molecule of product obtained. Thus, for each molecule of amine ester formed there may be one, two or more residues derived from the triethanolamine which contain a quaternisable nitrogen. The distribution obtained is entirely random and depends on factors such as the nature of the fatty acids and dicarboxylic acids used, the molar ratios of the reactants and the reaction conditions. Therefore, in the present description, reference is made to oligomeric amine esters, and it should be understood that this expression refers to products having a less or greater degree of oligomerisation, which depends on the factors already indicated.

The oligomeric amine esters so obtained can now be used, in the form of their salts, as a softening active substance which provides good results as regards its use in the preparation of textile-softening compositions. The salts can be obtained during the preparation of the softening composition, or prior thereto, by adding an inorganic or organic acid having sufficient strength to form the salt. Examples of suitable acids are hydrochloric acid, sulphuric acid, phosphoric acid and citric acid.

In order to obtain the quaternised products, it is possible to use methods which are already well known in the art of obtaining cationic surfactants derived from quaternary ammonium. For example, the reaction mixture resulting from the esterification is reacted with alkylating products, such as methyl chloride, methyl bromide, dimethyl sulphate, diethyl sulphate and dimethyl carbonate, preferably in the presence of organic solvents which facilitate its manipulation, such as isopropanol, ethanol propylene glycol, ethylene glycol, dipropylene glycol or fatty alcohols, and then the pH is adjusted to from 1.5 to 7.0, preferably to from 2 to 4.5, by the addition of a strong acid, such as any one of hydrochloric acid, sulphuric acid, phosphoric acid or citric acid.

The variation in the molar ratios of triethanolamine, fatty acids and dicarboxylic acids, within the margins defined by the present invention, enables products to be obtained which may be liquid, pasty or solid at ambient temperature.

The quaternised products obtained exhibit excellent properties as softeners of textile fibres, the properties being far superior to those exhibited by the products defined as preferred in DE-C-19539846 or appearing in its Examples.

The textile-softener composition comprises (a) a salt of the oligomeric amine ester as defined above or (b) the quaternized product of the oligomeric amine ester as defined above and water and/or any other solvent.

The mentioned compositions are aqueous dispersions or are solutions with solvents, for example, isopropanol, ethanol, propylene glycol, ethylene glycol, dipropylene glycol or butyl carbitol (trademark of diethylene glycol monoethyl ether) and/or water, which contain from 2% by weight to 45% by weight of the mentioned softening active substance, preferably from 4% by weight to 25% weight.

Optionally, the compositions may also contain, in any ratio, any other type of active product known as a textile-softener, especially other softening cationic surfactants, and more preferably other conventional esterquats, such as those mentioned above in the prior art section of the present description, or such as known ones of the imidazoline type.

The compositions forming the subject matter of the invention may also contain any type of optional ingredient known to be used in softening compositions as follows:

a) products which increase the efficiency of the compositions, such as fatty acids or fatty alcohols, silicones, amine oxides, anionic surfactants, such as lauryl ether sulphate or lauryl sulphate, amphoteric surfactants, such as cocoamidopropyl betaine or alkyl betaines, sulphosuccinates, fatty acid esters, ethoxylated glycerol esters, for example products from the LEVENOL (trademark) range supplied by Kao Corporation, S.A., polyglucoside derivatives, etc.; b) there may be used as stabilisers: salts of short-chain amines, which may or may not be quarternised, such as those of triethanolamine, N-methyldiethanolamine, etc., and also nonionic surfactants, such as ethoxylated fatty alcohols, ethoxylated fatty amines, ethoxylated alkyl phenols, etc.; c) for better control of viscosity, there may be used different inorganic salts, such as calcium chloride, magnesium chloride, calcium sulphate, sodium chloride, etc., or, in order to reduce the viscosity in concentrated compositions, compounds of the glycol type, such as, for example, ethylene glycol, dipropylene glycol, polyglycols, etc., and as thickeners for diluted compositions: polymers derived from cellulose, guar gum, etc., d) in order to adjust the pH, which must preferably be from 1.5 to 4.5, it is possible to use any type of inorganic and/or organic acid, such as hydrochloric acid, sulphuric acid, phosphoric acid, citric acid, etc.; e) it is also possible to use agents which improve soil release, such as known polymers or copolymers based on terephthalates; f) it is possible to use as preservatives: bactericidal products, such as formol, Kathon GC, Bronopol, etc.; g) finally, the compositions may also contain other products, such as antioxidants, colouring agents, perfumes, germicides, fungicides, anticorrosive agents, anticreasing agents, opacifiers, optical brighteners, pearlescent agents, etc.

The compositions forming the subject matter of the invention can be obtained simply by mixing their components until they disperse or dissolve, using methods well known to the person skilled in the art.

EXAMPLES

Examples 1 to 9

Preparation of salts of oligomeric amine esters and of the salts of their quaternised derivatives.

The products of Table 1 are prepared using the reactants in the amounts indicated in Table 1, in accordance with the following general methods:

Esterification. The fatty acid and the dicarboxylic acid and, optionally, as esterification catalyst, 0.75 g of 50% by weight hypophosphorous acid or 0.5 g of paratoluenesulphonic acid are mixed in a reaction flask equipped with an agitator, a temperature probe, and an inlet for an inert gas. The mixture is heated under an inert atmosphere to 100° C., the triethanolamine is added increasing the temperature to 170° C., and that temperature is maintained, while the water resulted from the esterification is distilled off, until the acidity index of the mixture is below 5 mg KOH/g.

Conversion into a salt. The product which results from the esterification and which is not to be quaternised is introduced, together with a sufficient amount of isopropyl alcohol to represent approximately from 8% to 12% by weight of the final product and, optionally, 0.75 g of BHT, into a reaction flask equipped with an agitator, a temperature probe and a charging funnel. The mixture is heated to 50° C. and, over a period of 1 hour, a 30% hydrochloric acid solution is added thereto in the stoichiometric amount necessary to convert all of the product into a salt, maintaing agitation at a temperature of 50–55° C. for a further 1–2 hours.

Quaternisation with methyl chloride. The product of the esterification stage which is to be quaternised is introduced, together with a sufficient amount of isopropyl alcohol to represent approximately from 8% to 12% by weight of the final product and, optionally, 0.75 g of BHT, into a reaction flask which is capable of working under pressure conditions and which is equipped with an agitator, a charging funnel and a temperature probe. The mixture is heated to 85–90° C. and an amount of methyl chloride slightly larger than the stoichiometric amount is added, maintaining the pressure at from 2–3 kg/cm$^2$. When the addition of methyl chloride is complete, the reaction mixture continues to be agitated at 80–85° C. for 1–2 hours.

Quaternisation with dimethyl sulphate. The product of the esterification stage which is to be quaternised is introduced, together with a sufficient amount of isopropyl and/or ethyl alcohol to represent from approximately 8% to approximately 12% by weight of the final product and, optionally, 0.75 g of BHT, into a 1 litre reaction flask equipped with an agitator, a temperature probe and a charging funnel. The mixture is heated to 50° C. and an a mount of dimethyl sulphate slightly smaller than the stoichiometric amount is addled slowly over a period of 1–2 hours. When the a ddition is complete, the reaction mixture is maintained at 50–55° C. for a further 3–4 hours.

TABLE 1

Examples 1 to 9

| Ex. | Fatty acid | Dicarboxylic acid | Triethanolamine | Quaternisation or conversion into salt |
|---|---|---|---|---|
| 1 | tallow 444.7 g(1.63 mol) + hydrogenated tallow 148.3 g(0.54 mol) | adipic 33.5 g (0.23 mol) | 171 g (1.15 mol) | quaternisation dimethyl sulphate |
| 2 | hydrogenated tallow 523 g(1.92 mol) | adipic 93.7 g (0.64 mol) | 191 g (1.28 mol) | quaternisation methyl chloride |
| 3 | tallow 429.8 g(1.58 mol) + hydrogenated tallow 141.2 g(0.52 mol) | PRIPOL 1009 ™ 60.1 g (0.22 mol) | 164.6 g (1.10 mol) | quaternisation dimethyl sulphate |
| 4 | hydrogenated tallow 348.2 g(1.28 g) + lauric 246.7 g(1.16 mol) | adipic 34 g (0.23 mol) | 173.4 g (1.16 mol) | quaternisation methyl chloride |
| 5 | hydrogenated tallow 523 g(1.92 mol) | adipic 93.6 g (0.64 mol) | 191 g (1.28 mol) | quaternisation dimethyl sulphate |
| 6 | 50% hydrogenated tallow 523 g(1.92 mol) | adipic 93.6 g (0.64 mol) | 186.7 g (1.25 mol) | quaternisation dimethyl sulphate |
| 7 | tallow 125.1 g(0.46 mol) + hydrogenated tallow 375.3 g(1.38 mol) | adipic 114.4 g(0.78 mol) | 195.8 g (1.31 mol) | quarternisation dimethyl sulphate |
| 8 | hydrogenated tallow 523 g(1.92 mol) | adipic 93.6 g (0.64 mol) | 191 g (1.28 mol) | conversion into salt hydrochloric ac. |
| 9 | tallow 564.7 g(2.08 mol) | adipic 67.4 g | 171.9 g | quaternisation |

TABLE 1-continued

Examples 1 to 9

| Ex. | Fatty acid | Dicarboxylic acid | Tri-ethanol-amine | Quaternisation or conversion into salt |
|---|---|---|---|---|
| | | (0.46 mol) | (1.15 mol) | dimethyl sulphate |

PRIPOL 1009™ is a dimeric fatty acid supplied by Unichema International

Comparative Examples C-1 to C-3

Preparation of conventional esterquats.

Using the general esterification methods described in Examples 1 to 9, but not using dicarboxylic acid, the conventional esterquats given in Table 2 are prepared.

TABLE 2

Comparative Examples C-1 to C-3

| Comparative Ex. | Fatty acid | Amine | Quaternisation |
|---|---|---|---|
| C-1 | tallow 454.3 g(1.67 mol) + hydrogenaed tallow 151.4 g(0.56 mol) | triethanol-amine 184.3 g (1.24 mol) | quaternisation dimethyl sulphate |
| C-2 | hydrogenaed tallow 650.7 g(2.39 mol) | N-methyl-diethanol-amine 142.3 g (1.20 mol) | quaternisation methyl chloride |
| C-3 | tallow 488 g(1.79 mol) + hydrogenaed tallow 162.7 g(0.60 mol) | N-methyl-diethanol-amine 142.3 g (1.20 mol) | quaternisation dimethyl sulphate |

Comparative Examples C-4 and C-5

Preparation of esterquats according to German patent DE-C-19539846.

In accordance with the methods described in Examples 1 and 2 of German patent DE-C-19539846, the products corresponding to those Examples, reffered to in the present description as Examples C-4 and C-5, respectively, are prepared.

Example 10

Softness tests on textiles.

The softness tests carried out on the products obtained in accordance with Examples 1 to 9 and Comparative Examples C-1 to C-5 are effected under conditions similar to those actually used commercially, comparing the results obtained at doses corresponding to two ratios of softening active substance based on the weight of the textile fibre: 0.1% and 0.2% dry weight of softening active substance relative to the weight of the fabric.

The tests are carried out on cotton towels, effecting five washes and five softening operations in the rinsing stage, one after each wash, using water of 25° HF (degrees French of hardness), in a MIELE™ washing machine and using the detergent marketed in Spain under the trade mark COLON™ by the Beckniser company.

The results are evaluated by calculating the statistical mean of the values obtained on the basis of quantification of the subjective opinion of 20 experienced panelists who use as references: a) a control which is given the value 0 and which is a cotton towel not treated with a softener after its washes; and b) a reference value which is assigned the value 10 and which corresponds to the softness result obtained with the product of Compative Example C-2, which is the conventional esterquat corresponding to the hydrogenated tallow fatty acid diester with N-methyldiethanolamine quaternised with methyl chloride.

The results obtained are indicated in Table 3.

TABLE 3

Softness tests on textiles

| Examples and com-parative examples | Molar ratio fatty ac./dicarboxylic ac. (FA/DA) | Molar ratio fatty ac. + dicarboxylic acid/triethanolamine (FA + DA/TEA) | Softness 0.1% active substance | Softness 0.2% active substance |
|---|---|---|---|---|
| 1 | 9.5:1 | 2.1:1 | 12 | 13 |
| 2 | 3:1 | 2:1 | 14 | 16 |
| 3 | 9.5:1 | 2.1:1 | 10 | 11 |
| 4 | 10.6:1 | 2.2:1 | 12 | 12 |
| 5 | 3:1 | 2:1 | 14 | 15 |
| 6 | 3:1 | 2:1 | 13 | 14 |
| 7 | 2.4:1 | 1.9:1 | 12 | 13 |
| 8 | 3:1 | 2:1 | 11 | 11 |
| 9 | 4.5:1 | 2.2:1 | 10 | 11 |
| C-1 | no dicaroboxylic acid | no dicaroboxylic acid | 8 | 8 |
| C-2 | no dicaroboxylic acid | no dicaroboxylic acid | 10 | 10 |
| C-3 | no dicaroboxylic acid | no dicaroboxylic acid | 9 | 9 |
| C-4 | 1.4:1 | 1.2:1 | 5 | 6 |
| C-5 | 2:1 | 1.5:1 | 6 | 7 |

Observation of the results set out in Table 3 clearly shows that the products constituting the softening active substance forming the subject matter of the invention, Examples 1 to 9, provide greater softness than do the conventional esterquats, Examples C-1 to C-3, and are far superior in that effect to the esterquats defined as being more advantageous or to those obtained in the Examples of DE-C-19539846, Examples C-4 and C-5.

Examples 11 to 20

Softening compositions.

The softening compositions indicated in Table 4 are prepared by conventional methods of mixing and agitation.

TABLE 4

Softening compositions

| Example | Softening active substance | LEVENOL C-642 ™ (% by weight) | Magnesium chloride (% by weight) | Minor components (colouring agent, perfume, preservative, ***and water) |
|---|---|---|---|---|
| 11 | 20% by wt. of product of Ex. 1 | — | 0.1 | qs for 100% by wt. |
| 12 | 5% by wt. of product of Ex. 1 | — | — | qs for 100% by wt. |
| 13 | 15% by wt. of product of Ex. 7 | — | 0.25 | qs for 100% by wt. |
| 14 | 5% by wt. of product of Ex. 7 | — | — | qs for 100% by wt. |
| 15 | 5% by wt. of product of Ex. 5 | — | 0.05 | qs for 100% by wt. |
| 16 | 5% by wt. of product of Ex. 9 | — | 0.1 | qs for 100% by wt. |
| 17 | 20% by wt. of product of Ex. 9 | — | 0.1 | qs for 100% by wt. |
| 18 | 16% by wt. of product of Ex. 9 | 4 | 0.1 | qs for 100% by wt. |
| 19 | 20% by wt. of product of Ex. 8 | — | 0.1 | qs for 100% by wt. |
| 20 | 14% bywt. of product of Ex. 8 and 6% by wt. of product of Ex. 6 | — | 0.25 | qs for 100% by wt. |

LEVENOL C-642™ is an ethoxylated glycerol ester marketed by Kao Corporation, S.A.

All the compositions of Table 4 exhibit excellent behaviour from the ponit of view of use as softeners for washed clothing in the rinsing stage. In addition, the viscosity of each composition remains stable over time.

What is claimed is:

1. A textile-softening agent comprising (a) a salt of an oligomeric amine ester obtained by esterifying triethanolamine with a mixture of a fatty acid and an aliphatic dicarboxylic acid at a molar ratio of the sum in total of the fatty acid and the dicarboxylic acid to triethanolamine ranging from 1.6:1 to 2.2:1 at a molar ratio of the fatty acid to the aliphatic dicarboxylic acid ranging from 2.2:1 to 11:1 or (b) a quaternized product of the oligomeric amine ester as defined above.

2. The agent as claimed in claim 1, in which the esterification is conducted at a molar ratio of the sum in total of the fatty acid and the dicarboxylic acid to triethanolamine ranging from 1.6:1 to 2.2:1 at a molar ratio of the fatty acid to the aliphatic dicarboxylic acid ranging from 2.5:1 to 10:1.

3. The agent as claimed in claim 1, in which the esterification is conducted at a molar ratio of the sum in total of the fatty acid and the dicarboxylic acid to triethanolamine ranging from 1.9:1 to 2.2:1 at a molar ratio of the fatty acid to the aliphatic dicarboxylic acid ranging from 2.5:1 to 4.5:1.

4. The agent as claimed in claim 1, in which the aliphatic dicarboxylic acid is shown by the formula: R—COOH, R being a linear or branched hydrocarbon chain having 7 to 23 carbon atoms, being saturated or unsaturated.

5. The agent as claimed in claim 1, in which the aliphatic dicarboxylic acid is shown by the formula:

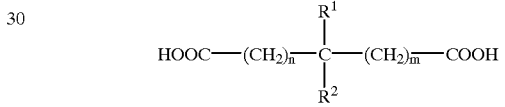

in which m and n are, independently of each other, an integer of zero to 17 and $R^1$ and $R^2$ are, independently of each other, a hydrogen atom or an alkyl of —$(CH_2)_p CH_3$, p being from 0 to 17.

6. The agent as claimed in claim 1, in which the aliphatic dicarboxylic acid is selected from the group consisting of adipic acid, sebacic acid, suberic acid, and dimeric fatty acids which are obtainable by thermal oligomerization of unsaturated fatty acids.

7. A textile-softener composition comprising (a) the salt of the oligomeric amine ester as defined in claim 1 or (b) the quaternized product of the oligomeric amine ester as defined in claim 1 and water and/or any other solvent.

8. The composition as claimed in claim 7, which comprises 2 to 45 percent by weight of (a) or (b).

9. The composition as claimed in claim 7, which further comprises any other softener.

10. The composition as claimed in claim 7, which further comprises a cationic surfactant known as an esterquat.

11. The agent as claimed in claim 1, wherein said molar ratio of the sum in total of the fatty acid and the dicarboxylic acid to triethanolamine ranges from 1.9:1 to 2.2:1.

12. A method for softening a textile, comprising contacting said textile with the agent as claimed in claim 1.

13. A process, comprising:
esterifying triethanolamine with a mixture of a fatty acid and an aliphatic dicarboxylic acid at a molar ratio of the sum in total of the fatty acid and the dicarboxylic acid to triethanolamine ranging from 1.6:1 to 2.2:1 at a molar ratio of the fatty acid to the aliphatic dicarboxylic acid ranging from 2.2:1 to 11:1, and optionally quaternizing, to obtain a textile-softening agent comprising (a) a salt of an oligomeric amine ester or (b) a quaternized product of said oligomeric amine ester.

14. A textile-softening agent comprising (a) a salt of an oligomeric amine ester obtained by esterifying triethanolamine:
(a) first with a fatty acid and then with an aliphatic dicarboxylic acid; or
(b) first with an aliphatic dicarboxylic acid and then with a fatty acid;
wherein a molar ratio of the sum in total of the fatty acid and the dicarboxylic acid to triethanolamine ranging from 1.6:1 to 2.2:1 at a molar ratio of the fatty acid to the aliphatic dicarboxylic acid ranging from 2.2:1 to 11:1 or (b) a quaternized product of the oligomeric amine ester as defined above.

15. The agent as claimed in claim 14, in which the esterification is conducted at a molar ratio of the sum in total of the fatty acid and the dicarboxylic acid to triethanolamine ranging from 1.6:1 to 2.2:1 at a molar ratio of the fatty acid to the aliphatic dicarboxylic acid ranging from 2.5:1 to 10:1.

16. The agent as claimed in claim 14, in which the esterification is conducted at a molar ratio of the sum in total of the fatty acid and the dicarboxylic acid to triethanolamine ranging from 1.9:1 to 2.2:1 at a molar ratio of the fatty acid to the aliphatic dicarboxylic acid ranging from 2.5:1 to 4.5:1.

17. The agent as claimed in claim 14, in which the aliphatic dicarboxylic acid is shown by the formula: R—COOH, R being a linear or branched hydrocarbon chain having 7 to 23 carbon atoms, being saturated or unsaturated.

18. The agent as claimed in claim 14, in which the aliphatic dicarboxylic acid is shown by the formula:

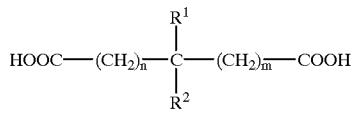

in which m and n are, independently of each other, an integer of zero to 17 and $R^1$ and $R^2$ are, independently of each other, a hydrogen atom or an alkyl of —$(CH_2)_p CH_3$, p being from 0 to 17.

19. The agent as claimed in claim 14, in which the aliphatic dicarboxylic acid is selected from the group consisting of adipic acid, sebacic acid, suberic acid, and dimeric fatty acids which are obtainable by thermal oligomerization of unsaturated fatty acids.

20. A method for softening a textile, comprising contacting said textile with the agent as claimed in claim 14.

21. The agent as claimed in claim 14, wherein said molar ratio of the sum in total of the fatty acid and the dicarboxylic acid to triethanolamine ranges from 1.9:1 to 2.2:1.

22. A textile-softener composition comprising (a) the salt of the oligomeric amine ester as defined in claim 14 or (b) the quaternized product of the oligomeric amine ester as defined in claim 1 and water and/or any other solvent.

23. The composition as claimed in claim 22, which comprises 2 to 45 percent by weight of (a) or (b).

24. The composition as claimed in claim 22, which further comprises any other softener.

25. The composition as claimed in claim 22, which further comprises a cationic surfactant known as an esterquat.

26. A process, comprising:
esterifying triethanolamine:
(a) first with a fatty acid and then with an aliphatic dicarboxylic acid; or
(b) first with an aliphatic dicarboxylic acid and then with a fatty acid;
wherein a molar ratio of the sum in total of the fatty acid and the dicarboxylic acid to triethanolamine ranging from 1.6:1 to 2.2:1 at a molar ratio of the fatty acid to the aliphatic dicarboxylic acid ranging from 2.2:1 to 11:1, and optionally quaternizing,
to obtain a textile-softening agent comprising (a) a salt of an oligomeric amine ester or (b) a quaternized product of said oligomeric amine ester.

* * * * *